United States Patent [19]

Lim et al.

[11] Patent Number: 4,861,840
[45] Date of Patent: Aug. 29, 1989

[54] NOVEL SILOXANYL ACRYLIC MONOMER AND GAS-PERMEABLE CONTACT LENSES MADE THEREFROM

[75] Inventors: Drahoslav Lim; Chidambar L. Kulkarni, both of San Diego, Calif.

[73] Assignee: Barnes-Hind, Inc., Sunnyvale, Calif.

[21] Appl. No.: 937,250

[22] Filed: Dec. 3, 1986

[51] Int. Cl.$^4$ .............................................. C08F 30/08
[52] U.S. Cl. ................................... 525/326.5; 526/279; 528/32; 524/91; 524/106
[58] Field of Search .................. 526/279; 528/32; 525/326.5; 524/91, 106

[56] References Cited

U.S. PATENT DOCUMENTS

| | | | |
|---|---|---|---|
| 3,548,025 | 12/1970 | Koerner | 260/824 |
| 3,808,178 | 4/1974 | Gaylord | 260/86.1 E |
| 4,120,570 | 10/1978 | Gaylord | 351/40 |
| 4,130,706 | 12/1978 | Plambeck | 526/245 |
| 4,139,513 | 2/1979 | Tanaka et al. | 260/29.6 TA |
| 4,139,548 | 2/1979 | Tanaka et al. | 260/448.2 B |
| 4,139,692 | 2/1979 | Tanaka et al. | 526/218 |
| 4,152,508 | 5/1979 | Ellis et al. | 526/279 |
| 4,216,303 | 8/1980 | Novicky | 528/32 |
| 4,246,389 | 1/1981 | LeBoeuf | 526/279 |
| 4,248,989 | 2/1981 | Novicky | 526/264 |
| 4,259,467 | 3/1981 | Keogh et al. | 526/279 |
| 4,303,772 | 12/1981 | Novicky | 526/279 |
| 4,314,068 | 2/1982 | Novicky | 556/440 |
| 4,330,383 | 5/1982 | Ellis et al. | 204/159.13 |
| 4,400,333 | 8/1983 | Neefe | 264/2.7 |
| 4,410,674 | 10/1983 | Ivani | 526/279 |
| 4,411,932 | 10/1983 | Kwan | 427/164 |
| 4,414,375 | 11/1983 | Neefe | 526/260 |
| 4,419,505 | 12/1983 | Ratkowski et al. | 526/279 |
| 4,424,328 | 1/1984 | Ellis | 526/279 |
| 4,433,125 | 2/1984 | Ichinohe et al. | 526/279 |
| 4,442,141 | 4/1984 | Lim | 427/164 |
| 4,450,264 | 5/1984 | Cho | 526/279 |
| 4,463,149 | 7/1984 | Ellis | 526/279 |
| 4,500,695 | 2/1985 | Ivani | 526/279 |
| 4,507,452 | 3/1985 | Foley | 526/279 |
| 4,508,884 | 4/1985 | Wittmann et al. | 526/279 |
| 4,535,138 | 8/1985 | Ratkowski et al. | 526/279 |
| 4,569,858 | 2/1986 | Lim et al. | 427/164 |
| 4,581,184 | 4/1986 | Powell | 264/2.6 |
| 4,582,884 | 4/1986 | Ratkowski | 526/279 |
| 4,602,074 | 7/1986 | Mizutani et al. | 526/245 |
| 4,611,039 | 9/1986 | Powell et al. | 526/271 |
| 4,612,358 | 9/1986 | Besecke et al. | 526/259 |
| 4,636,212 | 1/1987 | Posin et al. | 623/6 |

*Primary Examiner*—Melvyn I. Marquis
*Attorney, Agent, or Firm*—Scully, Scott, Murphy & Presser

[57] ABSTRACT

Disclosed are a novel monomer, and oxygen-permeable copolymers made therefrom, as well as contact lenses made from said copolymers, wherein the novel monomer has the formula:

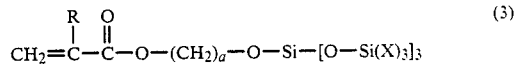

(3)

21 Claims, No Drawings

NOVEL SILOXANYL ACRYLIC MONOMER AND GAS-PERMEABLE CONTACT LENSES MADE THEREFROM

The present invention relates to a novel siloxane-acrylic monomer, to polymers made therefrom, and to contact lenses made from said polymers.

DESCRIPTION OF THE PRIOR ART

U.S. Pat. No. 4,314,068 discloses oxygen-permeable contact lenses made from a copolymer including a first comonomer with the following general formula (1):

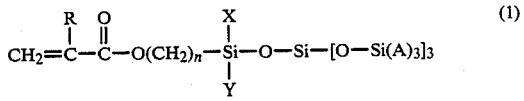
(1)

wherein R is selected from the group consisting of lower alkyl groups and hydrogen; n is an integer from about 1-3; X and Y are selected from the class consisting of lower alkyl groups, cycloalkyl groups, phenyl groups (substituted or unsubstituted), polysiloxanyl groups, fluorine and Z groups; Z is a group of the structure $-O-Si(OSi(A)_3)_3$; and wherein A is selected from the group consisting of lower alkyl groups and phenyl groups; a second comonomer which is an alkyl or cycloalkyl acrylate or methacrylate; a wetting component which can be acrylic or methacrylic acid, N-vinyl 2-pyrrolidone, or a hydroxyalkyl ester of acrylic or methacrylic acid; and a cross-linking agent such as an alkylene glycol dimethacrylate.

U.S. Pat. No. 4,152,508 discloses a silicone-containing hard contact lens material containing a first monomer having the formula (2):

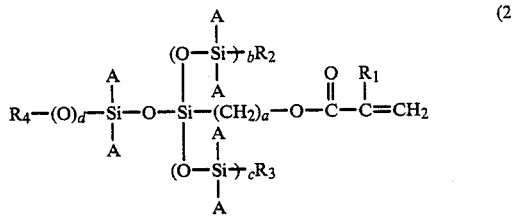
(2)

wherein $R_1$ is hydrogen or methyl, a is an integer from 1-3, b and c are integers from 0-2, d is 0 or 1, A is methyl or phenyl, $R_2$ is methyl or phenyl, and $R_3$ and $R_4$ represent either no group or methyl or phenyl groups; a second comonomer comprising an itaconate ester; a fracture strength adding material which is an ester of a $C_1$-$C_{20}$ monohydric or polyhydric alkanol, or phenol, and acrylic or methacrylic acid; a hydrophilic neutral, cationic or anionic monomer or ester thereof; and a cross-linking agent.

The present invention is characterized by a Si—O—C linkage which is expressly discouraged in U.S. Pat. No. 4,259,467, column 2, in the context of siloxanyl-di-acrylic compounds. This teaching in the '467 patent confirms that the superiority of the present invention is unexpected.

BRIEF SUMMARY OF THE INVENTION

The present invention comprises, in part, a novel monomer having the following formula (3):

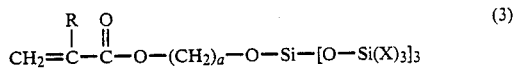
(3)

wherein each X independently represents a $C_1$-$C_6$ alkyl or phenyl group, a is an integer from 1-6, and R is hydrogen or methyl.

The present invention further comprises copolymers of a comonomer according to formula (3); a lower alkyl or cycloalkyl acrylate or methacrylate; a fluorinated or polyfluorinated $C_1$-$C_6$ alkyl methacrylate or acrylate; and a cross-linking component.

The present invention further comprises contact lenses made from the above-mentioned copolymer.

Another novel aspect of the present invention comprises an ultraviolet-absorbing compound which is a copolymer of 3-(2-benzotriazolyl)-2-hydroxy-5-tert-octyl-benzyl methacrylamide with the monomer of formula (3) and one or more of the other comonomers described herein.

DETAILED DESCRIPTION OF THE INVENTION

The novel copolymers including the novel comonomer of the present invention are useful in making contact lenses having many desirable attributes including oxygen permeability, machinability, and capability to exhibit good wettability in finished articles. The novel comonomer imparts these properties to the copolymer and articles made therefrom.

In the preferred embodiment of the novel comonomer identified above as formula (3), each radical X is lower alkyl and more preferably methyl. In an even more preferred embodiment, a equals 1-3 and more preferably 2. The monomer most preferred is tris(trimethylsiloxy)siloxyethyl methacrylate.

The novel comonomers of the present invention can be prepared for instance by reaction of tris(trialkylsiloxy)chlorosilane or tris(triphenylsiloxy)chlorosilane with hydroxyalkyl acrylate or hydroxyalkyl methacrylate in an inert solvent. A more detailed description of the preparation of the preferred comonomer is given below.

Representative second comonomers useful in making the useful copolymers of the present invention include the following: methylmethacrylate (preferred); ethylmethacrylate; ethylacrylate; or propyl, isopropyl, butyl, sec-butyl, pentyl, hexyl, heptyl, octyl, 2-ethyl hexyl, nonyl, decyl, undecyl, dodecyl, lauryl, cetyl, octadecyl, benzyl, phenyl or cycloalkyl acrylate or methacrylate. The alkyl substituent preferably has 1 to 6 carbon atoms. Representative cycloalkyl groups include cyclopropyl, cyclobutyl, cyclopentyl, cyclohexyl, cycloheptyl, and cyclooctyl.

The third comonomer in the useful copolymers of the present invention is a fluorinated or polyfluorinated ($C_1$-$C_6$) acrylate or methacrylate, preferably one in which up to 8 hydrogen atoms (preferably 3 to 8) are replaced by fluorine atoms. The preferred example is trifluoro ethyl methacrylate ($CF_3-CH_2-O-C(O)-C(CH_3)=CH_2$). Other comonomers which would perform the equivalent function include the following: pentafluoropropyl methacrylate, heptafluoro methylmethacrylate, hexafluoro isopropyl methacrylate and similar compounds.

The copolymer of the present invention also contains a cross-linking monomer having difunctional reactive sites, such as ethylene glycol dimethacrylate (preferred); diethylene glycol dimethacrylate; triethylene glycol dimethacrylate; tetraethylene glycol dimethacrylate; and other compounds known to those skilled in the art for use in cross-linking compounds of the type referred to herein.

The copolymer of the present invention is prepared by mixing together the four components indicated above, preferably in the following ranges: about 30 to about 60 weight percent of the comonomer of formula (3); about 5 to about 25 weight percent of the second comonomer; about 15 to about 35 weight percent of the fluorinated comonomer; and about 5 to about 15 percent of the ethylene glycol dimethacrylate and equivalent cross-linking agent.

The preferred concentration of the component of formula (3) is 45 to 60 weight percent, and more preferably about 50 weight percent. The preferred concentration of the second comonomer is about 5 to about 20 weight percent, and more preferably about 15 weight percent. The preferred concentration of the trifluoroethyl methacrylate or equivalent comonomer is about 20 to about 35 weight percent, and more preferably about 25 weight percent. The preferred concentration of the cross-linking agent is about 5 to 15 weight percent, more preferably about 10 weight percent.

Where it is desired that the copolymer's product have the ability to absorb ultraviolet radiation, a small but effective amount (typically up to about 5 weight percent) of an ultraviolet absorber is mixed together with the other monomers. The preferred copolymeric ultraviolet absorber is a copolymer made by copolymerizing a monomeric ultraviolet absorber having polymerizable vinylic unsaturation with the same monomers from which the copolymeric product itself is made, thereby facilitating dissolution of the copolymeric ultraviolet absorber into the monomer mixture from which the copolymeric product is made. For instance, a macromolecular product can be formed by copolymerizing a mixture of 20–40 wt% of a UV absorber such as 3-(2-benzotriazolyl)-2-hydroxy-5-tert-octylbenzyl methacrylamide, 20–40 wt% of a comonomer of formula (3) such as tris(trimethylsiloxy)siloxyethyl methacrylate, and 20–40 wt% of 2,2,2-trifluoroethyl methacrylate, or other fluorinated comonomer as defined herein, and optionally 20–40 wt% of an alkyl or cycloalkyl acrylate or methacrylate as defined above. Free radical copolymerization of the mixture using the initiator, amounts, and reaction conditions disclosed herein for the novel lens polymer, is preferred. An effective amount, preferably about 0.5 to about 0.2 weight, of the ultraviolet absorbing polymer (or another UV absorber such as or about 0.3 to about 1.0 weight percent of 2,2',4,4'-tetrahydroxy benzophenone, 2,2'-dihydroxy, 4,4'-dimethoxy benzophenone or 2,2' dihydroxy-4-methoxy benzophenone) can be added to impart ultraviolet absorbing ability to the resulting material. The absorber preferably absorbs some or all of the radiation in the range 350–450 nm, or preferably 300–450 nm. The ultraviolet absorber becomes dispersed in the copolymer and is physically entrapped therein, thereby resisting leaching of the absorber from lenses.

In making the copolymers of the present invention, a minor but effective amount such as 0.1–0.75 weight percent of a free radical initiator such as tert-butyl peroxyneodecanoate, tert-butyl peroctoate, or tert-butyl perbenzoate is added to the monomer mixture described above. The resulting mixture is then placed in a waterbath, or in an oven under nitrogen atmosphere. The effective polymerization temperature of from about 35° C. to about 110° C. is maintained for sufficient time, such as 170 hours, to permit the polymerization to proceed to completion.

The resulting clear, hard solid can then be relathed to form a rod, which is cut in the conventional way into buttons which are then machined to form contact lenses using known machining techniques. The resultant lenses exhibit the properties described above to a superior degree not heretofore expected.

Another aspect of the present invention is the treatment of lenses made from a copolymer containing one or more siloxanyl moieties of the formula —O—$SiD_1D_2D_3$ wherein $D_1$, $D_2$ and $D_3$ are independently $C_1$-$C_{10}$ alkoxy, $C_1$-$C_{10}$ alkyl, a phenyl ring, or another —$SiD_1D_2D_3$ group, pendant from a polymeric backbone of repeating acrylic or methacrylic units to render the copolymer surface more wettable by water or isotonic saline solution. The lens is treated with an aqueous solution of an agent which is a strong acid, or less preferably is a strong base. The agent cleaves siloxanyl groups from the lens surface and leaves hydroxyl groups in their place, thereby increasing the wettability of the lens surface. Suitable agents for increasing the wettability include sodium, potassium and ammonium bisulfate, sulphuric acid, and arylsulfonic acids such as toluenesulfonic acid.

This process increases the wettability of lenses made from the copolymers of the present invention. It is also useful with lenses containing pendant siloxanyl moieties derived from any of the siloxanyl-acrylic compounds disclosed in any of the following U.S. Pat. Nos.: 4,314,068; 4,152,508; 4,259,467; 3,808,178; 4,120,570; 4,139,513; 4,139,692; 4,216,303; 4,246,389; 4,330,383; 4,400,333; 4,410,674; 4,414,375; 4,419,505; 4,424,328; 4,433,125; 4,463,149; 4,500,695; 4,507,452; 4,508,884; 4,535,138; 4,581,184; 4,582,884; and 4,602,074, the disclosures of which are hereby incorporated herein by reference.

This process comprises reacting the surface of a lens or other material with an aqueous solution of an effective agent, such as one of those defined above, under conditions of time and temperature effective to replace pendant siloxanyl groups with hydroxyl groups on the surface of the article. Typically, times of 1 to 10 hours are satisfactory, with 2–6 hours preferred. Temperatures of typically 40° C.–80° C. are effective. Within these parameters, one skilled in this art can readily determine the concentration of the agent of choice which is effective to cause the desired degree of improvement in wettability. In general, higher concentrations require shorter reaction times.

The following examples are included for purposes of illustration and should not be considered limiting.

EXAMPLE 1

This example illustrates the synthesis of tris(trimethylsiloxy)siloxyethyl methacrylate.

2-Hydroxyethyl methacrylate (315 g) and pyridine (286 g) were placed in a three liter round bottom flask equipped with overhead stirrer, dropping funnel, drying tube, and thermometer. After cooling the flask in an ice-water bath to 12°–15° C., tris(trimethylsiloxy)-chlorosilane (400 g) was added with stirring over a 60 minute period while maintaining a temperature below 15° C. After the addition was over, the contents were stirred for 16 hours at room temperature.

Pentane (150 ml) was added to the mixture and pyridinium hydrochloride was filtered out and washed with some more pentane. The entire filtrate was extracted successively with water, 10% aq. acetic acid solution, water, 10% aq. sodium bicarbonate solution, and water. After drying the organic layer over anhydrous magnesium sulfate and filtering, the solvent was removed under reduced pressure. The colorless residual liquid was distilled under vacuum with 300 mm Claisen Vigreux distillation head and with 3% cuprous chloride as inhibitor. The fraction boiling at 87°-90° C. at about 10 m-torr pressure yielded 385 g (75%) of the title monomer. It was refrigerated until used.

EXAMPLE 2

This example illustrates the preparation of a copolymer made with the novel siloxanyl ester of Example 1.

A polymerization mixture was prepared by mixing 150 parts of tris(trimethylsiloxy)siloxy ethyl methacrylate (monomer of Example 1), 15 parts methyl methacrylate, 90 parts 2,2,2-trifluoroethylmethacrylate, 45 parts ethylene glycol dimethacrylate, 4.27 parts of a copolymeric UV absorber (made from previously copolymerizing 1.5 parts of 3-(2-benzotriazolyl)-2-hydroxy-5-tert-octylbenzyl methacrylamide with 0.64 parts tris(-trimethylsiloxy)siloxy-ethyl methacrylate and 2.13 parts of 2,2,2-trifluoroethyl methacrylate in toluene solution with tert-butyl peroxyneodecanoate and tert-butyl peroctoate as organic initiators), 0.018 parts D & C green #6, and organic peroxide initiators, 0.45 parts t-butyl peroxyneodecanoate, 0.45 parts t-butyl peroctoate and 0.45 parts t-butyl perbenzoate. Then the mixture was poured into foot-long high density polyethylene tubes (ID ⅜"), and polymerized under nitrogen blanket. The polymerization was effected by initially heating the tubes at 35° C. in a waterbath for 48 hours and then at 45° C. for 24 hours. Then these tubes were placed in a forced air oven and heating was continued at 85° C. for 24 hours, 100° C. for 56 hours and finally at 110° C. for 12 hours. The resulting polymeric rods were cut into lens blanks. The lenses obtained by lathing the blanks had excellent mechanical properties and oxygen permeability, DK 82 Barrer units at 35° C.

EXAMPLE 3

This example illustrates the preparation of another copolymer made with the novel siloxanyl ester of Example 1.

A polymerization mixture was prepared by mixing 60 parts of tris(trimethylsiloxy)siloxy-ethyl methacrylate, 5 parts methylmethacrylate, 25 parts 2,2,2'-trifluoroethyl methacrylate, 10 parts ethylene glycol dimethacrylate, 1.42 parts of a copolymeric UV absorber (made by previously copolymerizing 3-(2-benzotriazolyl)-2-hydroxy-5-tert-octyl benzyl methacrylamide with tris(-trimethylsiloxy)siloxyethyl methacrylate, and 2,2,2-trifluoroethylmethacrylate as described in Example 2), 0.003 parts D & C green #6, and organic peroxide initiators, 0.15 parts t-butyl peroxyneodecanoate, 0.15 parts t-butyl peroctoate and 0.15 parts t-butyl perbenzoate. The mixture was polymerized in foot-long high density polyethylene tubes (ID ⅜") and lenses were prepared as described in Example 2. The lenses obtained had excellent mechanical properties and oxygen permeability, DK 125 Barrer units at 35° C.

EXAMPLE 4

This example illustrates one of the methods employed to modify the surface of finished articles to enhance their wettability.

The finished lenses made from the copolymer of Example 2 were treated with a 66% solution of ammonium bisulfate in water and heated at 50° C. for four hours. The lenses were thereafter rinsed in water, 5% solution of sodium bicarbonate and water successively. Then, these lenses were stored in wetting and soaking solution. The wettability was measured by determining the soak state wetting angle of contact lens material. The wetting angle of 65° (±4) for untreated and 30° (±4) for treated material was observed. These reported numbers are the average of ten bubbles measured left and right sides for each of the three disks employed. A lower wetting angle value indicates better wetting characteristics.

What is claimed is:

1. A contact lens made of a copolymer of a compound having the formula:

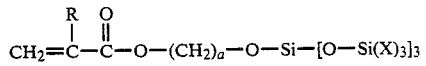

wherein each X is independently a straight or branched-chain alkyl group containing 1-6 carbon atoms, or phenyl; a is an integer from 1-6; and R is hydrogen or methyl.

2. A contact lens made of a compound in accordance with claim 1 wherein each X is independently a straight or branched-chain alkyl group containing 1-6 carbon atoms.

3. A contact lens made of a compound in accordance with claim 2 wherein a is 1, 2, or 3.

4. A contact lens made of a compound in accordance with claim 3 wherein each X is methyl and a is 2.

5. A contact lens made of a hard, oxygen-permeable copolymer comprising an addition polymer which is the reaction product of a composition comprising:
    (a) a compound in accordance with claim 1;
    (b) a $C_1$-$C_{18}$-alkyl, cyclo-$C_3$-$C_8$-alkyl, phenyl or benzyl acrylate or methacrylate;
    (c) a fluorinated $C_1$-$C_6$ alkyl methacrylate or acrylate substituted with at least 3 fluorine atoms; and
    (d) a cross-linking agent.

6. A contact lens made of a copolymer in accordance with claim 5 wherein component (a) is tris(trimethylsiloxy)siloxyethyl methacrylate.

7. A contact lens made of a copolymer in accordance with claim 6 wherein component (b) is a $C_1$-$C_6$ alkyl acrylate or methacrylate.

8. A contact lens made of a copolymer in accordance with claim 5 wherein component (a) is present in the amount of about 30 to about 60 weight percent; component (b) is present in the amount of about 5 to about 25 weight percent; component (c) is present in the amount of about 15 to about 35 weight percent; and component (d) is present in the amount of about 5 to about 15 weight percent.

9. A contact lens made of a clear, hard, oxygen-permeable copolymer comprising an addition polymer of the following composition:
    (a) about 30 to about 60 weight percent of tris(trimethylsiloxy)siloxyethyl methacrylate;

(b) about 5 to about 25 weight percent of methyl methacrylate;
(c) about 15 to about 35 weight percent of trifluoroethyl methacrylate; and
(d) about 5 to about 15 weight percent of a crosslinking agent.

10. A contact lens made of a clear, hard, oxygen-permeable copolymer comprising an addition polymer of the following composition:
   (a) about 45 to about 60 weight percent of tris(trimethylsiloxy)siloxyethyl methacrylate;
   (b) about 5 to about 20 weight percent of methyl methacrylate;
   (c) about 20 to about 35 weight percent of trifluoroethyl methacrylate; and
   (d) about 5 to about 15 weight percent of a crosslinking agent.

11. A compound useful as an ultraviolet absorber and comprising an addition polymer which is the reaction product of a composition comprising:
   (a) 3-(2-benzotriazolyl)-2-hydroxy-5-tert-octylbenzyl methacrylamide;
   (b) a compound having the formula

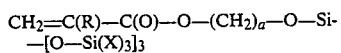

wherein each X is independently a straight or branched alkyl group containing 1-6 carbon atoms, or phenyl; a is an integer from 1-6; and R is hydrogen or methyl; and
   (c) a fluorinated $C_1$–$C_6$ alkyl acrylate or methacrylate substituted with at least 3 fluorine atoms.

12. A compound according to claim 11 wherein in compound (b) each X is methyl; a is 2; and R is methyl.

13. A compound according to claim 11 wherein compound (c) is trifluoroethyl methacrylate.

14. A compound in accordance with claim 11 which is the reaction product of a composition in which components (a), (b), and (c) each comprise 20-40 wt.%.

15. A compound useful as an ultraviolet absorber comprising an addition polymer which is the reaction product of a composition comprising:
   (a) 3-(2-benzotriazolyl)-2-hydroxy-5-tert-octylbenzyl methacrylamide;
   (b) a compound having the formula

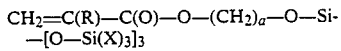

wherein each X is independently a straight or branched chain alkyl group containing 1-6 carbon atoms, or phenyl; a is an integer from 1-6; and R is hydrogen or methyl; and
   (c) a fluorinated $C_1$–$C_6$ alkyl acrylate or methacrylate substituted with at least 3 fluorine atoms; and
   (d) a $C_1$–$C_6$ alkyl or $C_3$–$C_8$ cycloalkyl acrylate or methacrylate.

16. A compound in accordance with claim 15 which is the reaction product of a composition in which components (a), (b), (c) and (d) each comprise 20-40 wt.%.

17. A contact lens made of a copolymer according to claim 5, further comprising up to about 2 weight percent of an ultraviolet absorbing additive which is an addition polymer which is the reaction product of 3-(2-benzotriazolyl)-2-hydroxy-5-tert-octylbenzyl methacrylamide, compound (a), and compound (c).

18. A contact lens comprising dispersed therein a compound according to claim 11 in an amount thereof effective to absorb ultraviolet radiation in the wavelength range of 300-450 nm.

19. A contact lens treated by a process for increasing the wettability of the surface thereof, said lens made from a homopolymer or copolymer of at least one acrylate or methacrylate monomer having pendant —O—$SiD_1D_2D_3$ groups, wherein $D_1$, $D_2$ and $D_3$ are independently $C_1$–$C_{10}$ alkyl, $C_1$–$C_{10}$ alkoxy, phenyl, or another —$OSiD_1D_2D_3$ group, comprising reacting said pendant groups with an agent capable of cleaving said groups, whereby the cleaved groups are replaced by hydroxyl groups.

20. The process of claim 19 wherein said object is a contact lens.

21. A contact lens treated by the process of claim 20.

* * * * *

UNITED STATES PATENT AND TRADEMARK OFFICE
CERTIFICATE OF CORRECTION

PATENT NO. : 4,861,840

DATED : August 29, 1989

INVENTOR(S) : Drahoslav Lim, et al.

It is certified that error appears in the above-identified patent and that said Letters Patent is hereby corrected as shown below:

Column 8, line 17, Claim 15: "$C_{3-C8}$" should read as --$C_3$-$C_8$--

Signed and Sealed this

Twenty-first Day of August, 1990

Attest:

HARRY F. MANBECK, JR.

Attesting Officer   Commissioner of Patents and Trademarks